United States Patent
Kato et al.

[11] Patent Number: 6,002,011
[45] Date of Patent: Dec. 14, 1999

[54] CRYSTALS OF BENZIMIDAZOLE DERIVATIVES AND THEIR PRODUCTION

[75] Inventors: Masayasu Kato, Ashiya; Toru Ishida, Takarazuka, both of Japan

[73] Assignee: Takeda Chemical Industries, Ltd., Osaka, Japan

[21] Appl. No.: 09/009,959

[22] Filed: Jan. 21, 1998

Related U.S. Application Data

[63] Continuation of application No. PCT/JP97/04136, Nov. 13, 1997.

[30] Foreign Application Priority Data

Nov. 14, 1996 [JP] Japan .................................. 8-303361

[51] Int. Cl.$^6$ .................................................. C07D 401/12

[52] U.S. Cl. ........................................ 546/273.7; 514/338

[58] Field of Search .......................................... 546/273.7

[56] References Cited

U.S. PATENT DOCUMENTS 5,690,960 11/1997 Bengtsson et al. ..................... 424/480

FOREIGN PATENT DOCUMENTS

| | | |
|---|---|---|
| 0 174 726 A1 | 3/1986 | European Pat. Off. . |
| 0 302 720 A1 | 2/1989 | European Pat. Off. . |
| 2297550 | 7/1996 | United Kingdom . |
| WO 95/01977 | 1/1995 | WIPO . |

OTHER PUBLICATIONS

Labhasetaw et al., Drug Development and Industrial Pharmacy, 19(6),631–641 (1993).

Evans, An Introduction to Crystal Chemistry, p. 393–397, 1964.

*Primary Examiner*—Jane Fan
*Attorney, Agent, or Firm*—David G. Conlin; George W. Neuner

[57] ABSTRACT

A substantially solvent-free and stable crystal of the compound of the formula:

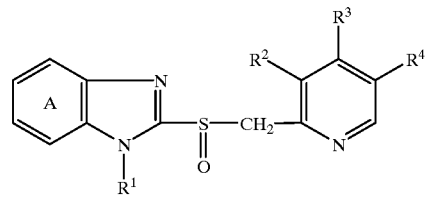

wherein the ring A may optionally be substituted, $R^1$ represents hydrogen or an N-protecting group, each of $R^2$, $R^3$ and $R^4$ (1) a hydrogen atom, (2) an alkyl group which may optionally be substituted with halogen atom(s) or (3) an alkoxy group which may optionally be substituted with halogen atom(s) or alkoxy; or its salt, is produced by subjecting a solvate of the compound (I) or its salt to de-solvent treatment, in an industrially advantageous method.

17 Claims, No Drawings

CRYSTALS OF BENZIMIDAZOLE DERIVATIVES AND THEIR PRODUCTION

This application is a continuation of copending application(s) International Application PCT/JP97/04136 filed on Nov. 11, 1997 and which designated the U.S.

TECHNICAL FIELD

The present invention provides crystals of benzimidazole derivatives which are of value as a medicine such as an anti-ulcer agent, and a method for producing the crystals.

BACKGROUND ART

Benzimidazole derivatives, i.e. 2-(2-pyridylmethylsulfinyl)benzimidazole derivatives which are of value as a medicine such as anti-ulcer agent, have been known in European Patent Application Publication No. 302720 (Japanese Patent Application Laid-open No. 1-131176), European Patent Application Publication No. 5129 (Japanese Patent Application Laid-open No. 58-192880), Japanese Patent Application Laid-open No. 61-22079, Japanese Patent Application Laid-open No. 64-6270, U.S. Pat. No. 4,255,431, European Patent Applicati,on Publication Nos. 45200, 74341, 80602, 174726, 175464, British Patent Application Publication No. 2134523.

European Application Publication No. 302720 (Japanese Patent Application Laid-open No. 1-131176) describes in Example 1 that 2-[[3-methyl-4-(2,2,2-trifluoroethoxy)pyridin-2-yl]methylsulfinyl]-benzimidazole was obtained as white crystals by subjecting a solution of 2-[[3-methyl-4-(2,2,2-trifluoroethoxy)pyridin-2-yl]methylthio]benzimidazole (monohydrate) in dichloromethane to an oxidation reaction with hydrogen peroxide using vanadium pentoxide as a catalyst, concentrating the reaction mixture, adding ethanol-water (9:1) to the residue, recovering the resulting crystals by filtration, rinsing them, dissolving this crystal crop in ethanol-water (9:1) at an elevated temperature (65–70° C.), filtering the solution when hot, cooling the filtrate with ice, recovering the resulting crystals by filtration, rinsing them, and drying them in vacuo.

Any compound in the 2-(2-pyridylmethylsulfinyl)-benzimidazole derivatives tends to lose stability and undergo decomposition when it contains traces of a solvent, particularly water, in its crystal structure and, therefore, this residual solvent in the crystal must be reduced to a minimum.

However, when the production procedure for 2-[[3-methyl-4-(2,2,2-trifluoroethoxy)pyridin-2-yl]-methylsulfinyl]benzimidazole as described in said EP-302720 is followed, water and ethanol can hardly be eliminated from the product and the resulting crystals inevitably contain fair amounts of water and ethanol. Thus, the benzimidazole compound provided by the process described in the above literature is a solvate containing one molecule each of water and ethanol and it is very difficult to desolvate the compound by vacuum drying without detracting from the stability of the product.

There is a serious problem with the above benzimidazole compound in the form of a solvate, particularly a hydrate, for being heat-labile, it is easily decomposed in the vacuum drying step, particularly under heating, thus depressing the purity of the product benzimidazole compound. Therefore, there has been an outstanding demand for a supply of solvent-free crystals of said benzimidazole compound and development of a high-production-scale, highly workable, and effective desolvation technology for providing such crystals.

DISCLOSURE OF INVENTION

In view of the above state of the art, the inventors of the present invention did an intensive investigation directed to improvements in the above-mentioned aspects for the purpose of providing substantially solvent-free crystals of said benzimidazole compound which is of value as a medicine, for example an anti-ulcer agent and so forth, and a high-production-scale, highly workable, and effective desolvation technology for providing such crystals. As a consequence, they discovered to everybody's surprise that the desired desolation can be easily achieved by oxidizing said 2-(2-pyridylmethylthio)benzimidazole compound to the corresponding 2-(2-pyridylmethyl-sulfinyl)benzimidazole compound, recrystallizing the latter from aqueous alcohol to give water- and alcohol-solvate crystals of said 2-(2-pyridylmethylsulfinyl)-benzimidazole compound, and suspending and stirring the crystals in warm water, which procedure unexpectedly causes a transformation of said solvate crystals into substantially solvent-free crystals, followed by drying under reduced pressure. The inventors further discovered to their own surprise that the substantially solvent-free crystals of said benzimidazole compound thus obtained are remarkably stable as compared with the conventional benzimidazole solvate, and completely free from decomposition in the course of vacuum drying.

The present invention provides:

(1) A method for producing a substantially solvent-free crystal of the compound of the formula:

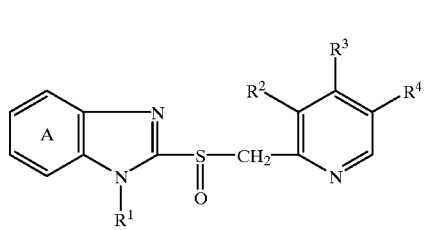

(I)

wherein the ring A may optionally be substituted, $R^1$ represents hydrogen or an N-protecting group, each of $R^2$, $R^3$ and $R^4$ is (1) a hydrogen atom, (2) an alkyl group which may optionally be substituted with halogen atom(s) or (3) an alkoxy group which may optionally be substituted with halogen atom(s) or alkoxy; or its salt, which comprises subjecting a solvate of the compound (I) or its salt to de-solvent treatment.

(2) The method as in the item (1), wherein the de-solvent treatment is to suspend the compound in water, (3) The method as in the item (1), wherein the N-protecting group in the compound (I) is an alkyl group, an acyl group, a carboalkoxy group, a carbamoyl group, an alkylcarbamoyl group, a dialkyl carbamoyl group, an alkylcarbonylmethyl group, an alkoxycarbonylmethyl group or an alkylsulfonyl group, (4) The method, as in the item (1), wherein $R^1$ in the compound (I) is a hydrogen atom, (5) The method as in the item (1), wherein the substituent on the ring A of the compound (I) is an alkoxy group which may optionally be substituted by halogen, (6) The method as in the item (1), wherein the ring A of the compound (I) is unsubstituted, (7) The method as in the item (1), wherein $R^2$ is methyl or methoxy, $R^3$ is $C_{1-4}$ alkyl which may optionally be substituted by fluorine(s) or $C_{1-4}$ alkoxy-$C_{1-8}$ alkoxy, $R^4$ is a hydrogen atom or methyl, (8) The method as in the item (1), wherein the compound (I) is 2-[[3-methyl-4-(2,2,2-trifluoroethoxy)-pyridin-2-yl]methylsulfinyl]benzimidazole, (9) A substantially solvent-free crystal of the compound of the formula:

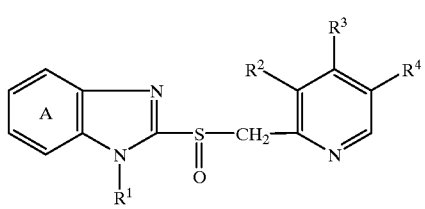

(I)

wherein the ring A may optionally be substituted, $R^1$ represents hydrogen or an N-protecting group, each of $R^2$, $R^3$ and $R^4$ is (1) a hydrogen atom, (2) an alkyl group which may optionally be substituted with halogen atom(s) or (3) an alkoxy group which may optionally be substituted with halogen atom(s) or alkoxy; or its salt, and

(10) The crystail as in the item (9), wherein the compound (I) is 2-[[3-methyl-4-(2,2,2-trifluoroethoxy)-pyridin-2-yl]methylsulfinyl]benzimidazole.

BEST MODE FOR CARRYING OUT THE INVENTION

The various definitions relevant to the above chemical formula and the present invention in general and preferred examples of species meeting the definitions are now presented.

Referring to formula (1), the optional substituent on ring A includes but is not limited to halogen, alkyl, cyano, carboxy, alkoxycarbonyl, carboalkoxyalkyl, carbamoyl, carbamoylalkyl, hydroxy, alkoxy, hydroxyalkyl, halogenated alkyl, halogenated alkoxy, acyl, carbamoyloxy, nitro, acyloxy, aryl, aryloxy, alkylthio, and alkylsulfinyl.

The halogen mentioned above includes fluorine, chlorine, bromine, etc., with fluorine being particularly preferred.

The alkyl mentioned above is preferably alkyl of 1 to 7 carbon atoms, such as methyl, ethyl, propyl, isopropyl, butyl, isobutyl, pentyl, hexyl, and heptyl.

The alkoxycarbonyl mentioned above is preferably one containing 1 to 4 carbon atoms in the alkoxy moiety, including methoxycarbonyl ($CH_3OOC$—) and ethoxycarbonyl ($C_2H_5OOC$—), among others.

The carboalkoxyalkyl mentioned above is preferably one containing 1 to 4 carbon atoms in each of its alkoxy and alkyl moieties, thus including carbomethoxymethyl ($CH_3OOCCH_2$—), carbomethoxyethyl ($CH_3OOCC_2H_4$—), carboethoxymethyl ($C_2H_5OOCCH_2$—), and carboethoxyethyl ($C_2H_5OOCC_2H_4$—), among others.

The carbamoylalkyl mentioned above is preferably one containing 1 to 4 carbon atoms in its alkyl moiety, including carbamoylmethyl ($H_2NCOCH_2$—) and carbamoylethyl ($H_2NCOC_2H_4$—), among others.

The alkoxy mentioned above is preferably one containing 1 to 5 carbon atoms, such as methoxy, ethoxy, propoxy, isopropoxy, butoxy, isobutoxy, and pentoxy.

The hydroxyalkyl mentioned above is preferably one containing 1 to 7 carbon atoms in its alkyl moiety, such as hydroxyinethyl, 1-hydroxy-propyl-2, 1-hydroxy-ethyl-2, and 1-hydroxy-2-methyl-propyl-2, among others.

The halogenated alkyl mentioned above is preferably one containing 1 to 7 carbon atoms in its alkyl moiety, including difluoromethyl and trifluoromethyl, to name but a few preferred examples.

The halogenated alkoxy mentioned above is preferably one containing 1 to 4 carbon atoms in its alkoxy moiety, including difluoromethoxy as a typical preferred example.

The acyl mentioned above is preferably one containing 1 to 4 carbon atoms, such as formyl, acetyl, propionyl, butyryl, and isobutyryl.

The acyloxy mentioned above is preferably one containing 1 to 4 carbon atoms in its acyl moiety, including formyloxy, acetyloxy, propionyloxy, butyryloxy, and isobutyryloxy.

The aryl mentioned above includes but is not limited to phenyl, tolyl, and naphthyl.

The aryloxy mentioned above includes but is not limited to phenyloxy, tolyloxy, and naphthyloxy.

The alkylthio mentioned above is preferably one containing 1 to 6 carbon atoms in its alkyl moiety, including but not limited to methylthio, ethylthio, and propylthio.

The alkylsulfinyl mentioned above is preferably one containing 1 to 6 carbon atoms, including but not limited to methylsulfinyl, ethylsulfinyl, and propylsulfinyl.

Referring, further, to formula (1), ring A is preferably either unsubstituted or substituted by, among the above-mentioned substituent groups, halogen, alkyl, alkoxy, halogenoalkyl or halogenoalkoxy (more preferably such species as methoxy, trifluoromethyl or difluoromethoxy). Particularly preferred are cases in which such a substituent is present in the 4- or 5-position of the benzimidazole ring.

$R^1$ in formula (1) represents hydrogen atom or an N-protecting group.

The N-protecting group for $R^1$ includes but is not limited to alkyl, acyl, carboalkoxy, carbamoyl, alkylcarbamoyl, dialkylcarbamoyl, alkylcarbonylmethyl, alkoxycarbonylmethyl and alkylsulfonyl.

The alkyl mentioned just above is preferably one containing 1 to 5 carbon atoms, including methyl, ethyl, propyl, isopropyl, butyl, isobutyl and pentyl.

The acyl includes the same species as mentioned for the substituent on ring A.

The carboalkoxy includes the same species as mentioned for the substituent on ring A.

The alkylcarbamoyl, which can be represented by the formula: alkyl-NH—CO—, is preferably one containing 1 to 4 carbon atoms in its alkyl moiety, such as methylcarbamoyl, ethylcarbamoyl, propylcarbamoyl, isopropylcarbamoyl, etc.

The dialkylcarbamoyl, which can be represented by the formula: $(alkyl)_2N$—CO—, is preferably one containing 1 to 4 carbon atoms in each of its alkyl moieties, including dimethylcarbamoyl, diethylcarbamoyl, and N-methyl-N-ethylcarbamoyl, among others.

The alkylcarbonylmethyl, which can be represented by the formula: alkyl-CO—$CH_2$—, is preferably a group in which said alkyl contains 1 to 4 carbon atoms, such as acetylmethyl and propionylmethyl, among others.

The alkoxycarbonylmethyl, which can be represented by the formula: alkyl-OCO—$CH_2$—, is preferably a group in which said alkyl contains 1 to 4 carbon atoms, thus including methoxycarbonylmethyl, ethoxycarbonylmethyl, and propoxycarbonylmethyl, among others.

The alkylsulfonyl, which can be represented by the formula: alkyl-$SO_2$—, is preferably one containing 1 to 4 carbon atoms in its alkyl moiety, including methylsulfonyl, ethylsulfonyl, propylsulfonyl, and isopropylsulfonyl, etc.

In formula (I), $R^1$ preferably represents hydrogen.

In formula (I), $R^2$, $R^3$, and $R_4$ are the same or different and each represents hydrogen, alkyl optionally substituted by halogen, or alkoxy optionally substituted by halogen, or alkoxy.

The alkyl of said alkyl optionally substituted by halogen as mentioned for $R^2$, $R^3$, and $R^4$ is preferably an alkyl group of 1 to 4 carbon atoms, such as methyl, ethyl, propyl, isopropyl, butyl, and isobutyl. The halogen of said alkyl optionally substituted by halogen includes fluorine, chlorine, bromine, etc. and is preferably fluorine.

The alkyl substituted by halogen is preferably fluorine-substituted alkyl such as trifluoromethyl, 2,2,2-trifluoroethyl, 2,2,3,3-tetrafluoropropyl, 2,2,3,3,3-pentafluoropropyl, 1-(trifluoromethyl)-2,2,2-trifluoroethyl, 2,2,3,3,4,4,4-heptafluorobutyl, etc., and as examples of chlorine- or bromine-substituted alkyl, too, the species available upon replacement of fluorine with chlorine or bromine in the species mentioned above for fluorine-substituted alkyl can be mentioned.

The alkyl optionally substituted by halogen as mentioned for $R^2$, $R^3$, and $R^4$ is preferably an unsubstituted alkyl group of 1 to 4 carbon atoms, with methyl being particularly preferred.

The alkoxy of said alkoxy optionally substituted by halogen or alkoxy as mentioned for $R^2$, $R^3$, and $R^4$ is alkoxy containing 1 to 8 carbon atoms, preferably 1 to 4 carbon atoms, including methoxy, ethoxy, propoxy, isopropoxy, butoxy, isobutoxy, pentoxy, hexyloxy, heptyloxy and octyloxy. The halogen of said alkoxy optionally substituted by halogen includes fluorine, chlorine, bromine, etc., with fluorine being particularly preferred.

The alkoxy substituted by halogen is alkoxy of 1 to 8 carbon atoms, preferably 1 to 4 carbon atoms, which are substituted by 1 to 8 (preferably 3 or 4) fluorine atoms, such as 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy, 2,2,3,3,4,4,5,5-octafluoropentoxy, etc. Particular preferred is 2,2,2-trifluoroethoxy or 2,2,3,3-tetrafluoropropoxy. With regard to chlorine- or bromine-substituted alkoxy, too, the species available upon replacement of fluorine with chlorine or bromine in the species mentioned above for fluorine-substituted alkoxy can be mentioned.

The alkoxy-substituted alkoxy includes $C_{1-4}$ alkoxy-$C_{1-8}$ alkoxy (particularly $C_{1-4}$ alkoxy-$C_{1-4}$ alkoxy) such as 3-methoxypropoxy, 2-methoxyethoxy, 3-ethoxypropoxy, 2-ethoxyethoxy, etc., with 3-methoxypropoxy being particularly preferred.

In formula (I), preferably $R^2$ and $R^4$ are the same or different and each represents hydrogen, methyl, or methoxy and $R^3$ represents alkoxy containing 1 to 5 carbon atoms, preferably 2 to 4 carbon atoms, which has been substituted by 3 to 4 halogen atoms, or methoxy.

Referring, further, to the compound of formula (I), the preferred specific compounds are such that ring A is unsubstituted or the 4- or 5-position of the benzimidazole ring is substituted by methoxy, difluoromethoxy, or trifluoromethyl, $R^1$ is hydrogen, $R^2$ is methyl or methoxy, $R^3$ is $C_{2-4}$ alkoxy substituted by 3 or 4 fluorine atoms, methoxy, or 3-methoxypropoxy, and $R^4$ is hydrogen or methyl.

The salt of the compound of formula (I) is preferably a pharmaceutically acceptable salt, which includes salts with inorganic bases, salts with organic bases, and salts with basic amino acids. Preferred salts with inorganic bases are salts with alkali metals such as sodium and potassium, salts with alkaline earth metals such as calcium and magnesium, and ammonium salts. Preferred salts with organic bases are salts with trimethylamine, triethylamine, pyridine, picoline, ethanolamine, diethanolamine, triethanolamine, dicyclohexylamine, and N,N'-dibenzylethylenediamine. Preferred salts with basic amino acids are salts with arginine, lysine, ornithine, etc. The preferred salt of the compound of formula (I) according to the present invention includes salts with alkali metal salts and alkaline earth metal salts. The sodium salt is particularly preferred.

Specifically, the compound of formula (I) includes but is not limited to:

2-[[3-methyl-4-(2,2,2-trifluoroethoxy)pyridin-2-yl]methylsulfinyl]benzimidazole, 2-[[3,5-dimethyl-4-methoxypyridin-2-yl]methylsulfinyl]-5-methoxybenzimidazole, 2-[[4-(3-methoxypropoxy)-3-methylpyridin-2-yl]methylsulfinyl]benzimidazole sodium salt, and 5-difluoromethoxy-2-[(3,4-dimethoxypyridin-2-yl)methylsulfinyl]benzimidazole.

Particularly preferred is 2-[[3-methyl-4-(2,2,2-trifluoroethoxy)pyridin-2-yl]methylsulfinyl]benzimidazole.

The benzimidazole compound of the formula (I) can be produced by manners described in the above-mentioned literatures, i.e. European Patent Application Publication No. 302720 (Japanese Patent Application Laid-open No. 1-131176), European Patent Application Publication No. 5129 (Japanese Patent Application Laid-open No. 58-192880), Japanese Patent Application Laid-open No. 61-22079, Japanese Patent Application Laid-open No. 64-6270, U.S. Pat. No. 4,255,431, European Patent Application Publication Nos. 45200, 74341, 80602, 174726, 175464, British Patent Application Publication No. 2134523, or analogous methods thereto.

The benzimidazole compound has an asynmmetric center at the sulfur atom. Namely it can be present as two types of isomers,

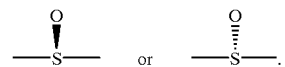

The above benzimidazole compound can be obtained as crystals of its water- and alcohol-solvate by recrystallization from the corresponding aqueous alcohol in accordance with, for example, the purification procedure disclosed in European Patent Application Publication No. 302720 (Japanese Patent Application Laid-open No. 1-131176) or any procedure analogous thereto. The alcohol mentioned above includes $C_{1-6}$ alcohols (e.g. methanol, ethanol, isopropyl alcohol, etc.), ethanol being particularly preferred. The aqueous alcohol may for example be one containing about 2 to about 30 parts by volume of an alcohol (especially ethanol), preferably about 5 to about 15 parts by volume of an alcohol (especially ethanol) for each part by volume of water. To be specific, a mixture consisting of an alcohol (especially ethanol) and water in a ratio of about 9:1, v/v can be used.

The crystals of such a solvate of the compound of formula (I) or its salt can be easily confirmed by the known analytical techniques such as powder X-ray diffraction analysis.

In accordance with the process of the invention, the solvate crystals mentioned above are suspended, left standing or stirred in water. As the result of this procedure, the solvate crystals are desolvated due to a morphological transformation. While the conditions of this leaving standing or suspending procedure, such as the quantity and temperature of water used and agitation time, can be selected judiciously, the following conditions may be typically mentioned. As to the quantity of water, water can be used in a proportion of about 2 to about 20 parts by volume, preferably about 5 to about 10 parts by volume, relative to the solvate crystals. The water temperature may range from room temperature (ca 15 to ca 30° C.) to about 90° C., preferably from about 30° to about 50° C. The agitation time may range from about 0.5 to about 5 hours, preferably from about 1 to about 2 hours.

The solvent-free crystals available upon said morphological transformation of solvate crystals are then collected by a per se known procedure, such as filtration, and dried, if necessary, by a per se known procedure, whereby the objective substantially solvent-free crystals of the particular benzimidazole compound are obtained. The drying procedure referred to above is preferably drying under reduced pressure or in vacuo, where the drying temperature may for example be about 20° to about 60° C., preferably about 30° to about 50° C., and the drying time may be about 5 to about 48 hours, preferably about 10 to about 20 hours.

It is understood that the water content of the substantially solvent-free crystals according to the present invention is not higher than about 500 ppm, preferably not higher than about 300 ppm, and, for still better results, not higher than about 200 ppm, and the alcohol (e.g. ethanol) content is not higher than about 200 ppm, preferably not higher about 100 ppm, and, for still better results, not higher about 80 ppm. The water content and alcohol content of the crystals depend on the conditions used in said suspending procedure and drying procedure (particularly the treating times) and, therefore, if the degree of desolvation is found to be insufficient, the duration of said suspending procedure and/or of said drying procedure can be extended so as to achieve more thorough desolvation.

The substantially solvent-free crystals of the compound of formula (1) or its salt as produced in the above manner can be easily verified by a known technique such as powder X-ray diffraction analysis and the water content and alcohol (ethanol) content thereof can be determined by per se known analytical procedures. Specifically, Karl-Fischer (KF) method may be mentioned for water content, and gas chromatography for alcohol content.

The substantially solvent-free crystals obtained above can be processed into the desired dosage forms by the routine pharmaceutical procedures and be put to use as medicines, for example, anti-ulcer agents. For pharmaceutical manufacture, the procedures described in the Reference Examples, for instance, can be employed.

The present invention is explained in detail in the following working examples, but is not limited to that illustrated in the Examples. In the following, water content was measured by the Karl-Fisher method, and alcohol content was measured by gas chromatography.

REFERENCE EXAMPLE 1
Production of 2,3-dimethylpyridine N-oxide

One hundred g. of 2,3-lutidine was dissolved into 200 ml. of glacial acetic acid, followed by dropwise addition of 120 g. of 35% aqueous hydrogen peroxide solution at about 40° C. The mixture was allowed to react at 105° C. for about 2 hours. After completion of the reaction, the mixture was cooled down to about 50° C., followed by addition of 5.0 g. of p-formaldehyde. The resultant mixture was heated to 105° C. to cause the reaction to take place for about 10 minutes. The resultant mixture was cooled down to about 40° C., followed by addition of 150 g. of 98% sulfuric acid. The resultant mixture was subjected to distillation under reduced pressure to evaporate the glacial acetic acid off to give 2,3-dimethylpyridine N-oxide as a sulfuric acid solution.

REFERENCE EXAMPLE 2
Production of 2,3-diemthyl-4-nitropyridine N-oxide

To the whole sulfuric acid solution of 2,3-dimethylpyridine N-oxide as obtained in Reference Example 1, were dropwisely added 130 g. of 98% sulfuric acid and 130 g. of 98% nitric acid at about 80° C. for 4 hours. The resultant mixture was allowed to react at the same temperature for 5 hours. The resultant mixture was cooled down to about 40° C. and poured into 1 L of cold water at below 5° C., followed by dropwise addition of 0.6 L of 30% sodium hydroxide solution at below 30° C. The resultant mixture was extracted three times, each with 1 L. methylenechloride. The obtained methylenechloride layers were pooled and concentrated under reduced pressure to give 2,3-dimethyl-4-nitropyridine N-oxide as a pale yellow crystalline residue. Yield:141 g. (90% based on 2,3-lutidine)

REFERENCE EXAMPLE 3
Production of 2,3-dimethyl-4-(2,2,2-trifluoroethoxy)-pyridine N-oxide To all the amount of 2,3-dimethyl-4-nitropyridine N-oxide which was obtained in Reference Example 2 was added 0.4 L. of 70% aqueous acetonitril solution to make a solution, followed by the addition of 280 g. of trifluoroethanol, 9 g. of a 50% aqueous benzyltributylammonium chloride solution and 225 g. of potassium carbonate. The mixture was allowed to react at a refluxing temperature for about 25 hours. The resultant mixture was cooled down to about 60° C., followed by addition of 0.2 L. of water. The resultant mixture was stirred and left standing. The resultant organic layer was taken by decantation and concentrated under reduced pressure. 0.5 L. of water was added to the concentrate to make it into a solution, followed by three extractions with 0.5 L. methylenechloride. The methylenechloride layer was pooled and concentrated to give 2,3-dimethyl-4-(2,2,2-trifluoroethoxy)pyridine N-oxide as pale yellow crystalline residue. Yield:144 g.(70% based on 2,3-lutidine).

REFERENCE EXAMPLE 4
Production of 2-hydroxymethyl-3-methyl-4-(2,2,2-trifluoroethoxy)pyridine(HYD)

Into 0.3 L. of glacial acetic acid was dissolved all the amount of 2,3-dimethyl-4-(2,2,2-trifluoroethoxy)pyridine N-oxide which was obtained in Reference Example 3, followed by addition of 0.3 L. of acetic anhydride. The resultant mixture was allowed to react at about 115° C. for about 6 hours. After completion of the reaction, the resultant mixture was cooled down to about 60° C., followed by addition of 0.3 L. of water. The resultant mixture was concentrated under reduced pressure, followed by addition of 25 ml. of methanol and 0.2 L. of water. To the resultant mixture was added dropwise 0.2 L. of 30% aqueous sodium hydroxide solution at about 30° C. to adjust its pH at 13, followed by stirring at about 35° C. for 12 hours.

The resultant mixture was left standing, and the supernatant was taken off. To the resultant residue was added 100 ml. of methanol, followed by stirring at about 45° C. for about 30 minutes to solubilize the precipitated crystals. While the resultant solution was kept at about 20° C., 0.5 L. of water was added in order to precipitate crystals. The resultant mixture was cooled down to about 5° C. and kept standing. The precipitated crystals were collected by filtration, washed with water and dissolved into a mixed solution of 75 ml. of 35% hydrochloric acid, 0.4 L. of water and 2.5 g. of diatomaceous earth. The resultant solution was adjusted to a pH of about 3 with a 30% aqueous sodium hydroxide solution, and the insolubles were filtered off. The filtrate was washed three times, each with 200 ml. of methylenechloride. After addition of 5.0 g. of activated charcoal, the mixture was stirred at about 40° C. for about 12 hours. The activated charcoal was filtered off, and 80 ml. of ethanol was added to the filtrate. The resultant mixture was neutralized to pH 7 with 30% aqueous sodium hydroxide solution to precipitate crystals. The mixture was cooled down to below 5° C., and the precipitated crystals were collected by filtration and washed with wacter. The obtained crystals were dried at about 37° C. under reduced pressure for about 24 hours to give 2-hydroxymethyl-3-methyl-4-(2, 2,2-trifluoroethoxy)pyridine as white crystals. Yield:95 g.(46% based on 2,3-lutidine).

REFERENCE EXAMPLE 5

Production of 2-[[[3-methyl-4-(2,2,2-trifluoroethoxy)-2-pyridyl]-methyl]thio]benzimidazole monohydrate 49.9 g. of 2-hydroxymethyl-3-methyl-4-(2,2,2-trifluoroethoxy)pyridine was dissolved into 0.4 L. of methylene-chloride, followed by dropwise addition of 24 ml. of thionylchloride for about 30 minutes. The mixture was allowed to react at more than about 30° C. for about 1 hour. After completion of the reaction, 0.1 L. of water was added, and the methylenechloride was evaporated off under reduced pressure. The residue was dissolved into 0.4 L. of methanol, followed by addition of 34.2 g. of 2-benzimidazolethiol. To the mixture was added dropwise 60 ml. of a 30% aqueous sodium hydroxide solution at about 25° C. for about 1 hour. The mixture was allowed to react at room temperature for about 0.5 hour. To the resultant mixture was added 0.3 L. of water, followed by stirring at below 10° C. for about 30 minutes. The resultant mixture was adjusted to a pH of about 9 with 35% hydrochloric acid in order to precipitate crystals. The resultant crystals were collected by filtration and washed with, in turn, 0.1 L. of 50% methanol and 0.2 L. of water. The obtained crystals were dried with hot air at below 50° C. to give 2-[[[3-methyl-4-( 2,2,2-trifluoroethoxy)-2-pyridyl]-methyl]thio] benzimidazole as white crystals. Yield:81.0 g. (96.7% based on HYD).

REFERENCE EXAMPLE 6

Production of 2-[[3-methyl-4-(2,2,2-trifluoroethoxy)-pyridin-2-yl]methylsulfinyl]benzimidazole monohydrate, monoethanol solvate.

Forty mg. of acetylacetone vanadium(IV) was dissolved in 150 ml. of ethanol, followed by addition of 20.0 g. of 2-[[3-methyl-4-(2,2,2-trifluoroethoxy)-pyridin-2-yl] methylthio]benzimidazole monohydride and further dropwise addition of 6.14 g. of 35% aqueous hydrogen peroxide solution at 20 to 25° C. The mixture was allowed to react at the same tempertaure for about 5 hours. After completion of the reaction, aqueous solution of sodium thiosulfate(2.7 g./16 ml.) was added, followed by vigorous stirring for about 10 minutes. The precipitated crystals were collected by filtration and washed with ice-cooled ethanol-water mixture (8:2). To the resultant crystals was added 90 ml. of ethanol-water mixture(9:1), and the mixture was heated to 60 to 70° C. under stirring to dissolve the crystals. The insolubles were filtered off while the mixture was hot. The filtrate was ice-cooled to precipitate crystals. The precipitated crystals were collected by filtration, washed with ice-cooled ethanol-water(8:2) and dried under reduced pressure at room temperature to give 2-[[3-methyl-4-(2,2,2-trifluoroethoxy) pyridin-2-yl]methylsulfinyl]-benzimidazole monohydrate, monoethanolate solvate as white needles. Yield:21.2 g.(91.0%).

EXAMPLE 1

Production of 2-[[3-methyl-4-(2,2,2-trifluoroethoxy)-pyridin-2-yl]methylsulfinyl]benzimidazole substantially free from solvent(hereinafter sometimes abbreviated to as Compound A.

To 75 ml. of ethanol-water mixture(9:1) was added 70 μl. of 25% atqueous ammonia solution. While the solution was heated to about 60° C., 13.0 g. of 2-[[3-methyl-4-(2,2,2-trifluoroethoxy)pyridin-2-yl]methylsulfinyl]benzimidazole monohydrate, monoethanolate solvate which was obtained in Reference Example 6, was added to the solution to be dissolved. The insolubles were removed by filtration off while the solution was hot. The filtrate was cooled with ice to precipitate crystals. The precipitated crystals were collected by filtration to give wet crystals of 2-[[3-methyl-4-(2,2,2-trifluoroethoxy)pyridin-2-yl]methylsulfinyl] benzimidazole monohydrate, monoethanolate solvate. Thus obtained wet crystals were suspended in 53 ml of water and the suspension was stirred for 1 hour while keeping the temperature at 30° C. The emerged crystals were recovered by filtration, washed with 10 ml of water, and then were dried at 40° C. in vacuum for 10 hours to give 2-[[3-methyl-4-(2,2,2-trifluoroethoxy)pyridin-2-yl]-methylsulfinyl]benzimidazole as white needles.

Yield:9.72 g.(87.7%). m. p. 177–178(decomp.). Water content:0.01%. Ethanol content:63 ppm.

COMPARATIVE EXAMPLE 1

Production of 2-[[3-methyl-4-(2,2,2-trifluoroethoxy)-pyridin-2-yl]methylsulfinyl] benzimidazole by a known method.

To 58 ml. of ethanol-water mixture(9:1) was added 54 μl. of 25% aqueous ammonia solution. The mixture was heated to about 60° C., followed by addition of 10.0 g. of 2-[[3-methyl-4-(2,2,2-trifluoroethoxy)pyridin-2-yl] methylsulfinyl]benzimidazole monohydrate, monoethanolate solvate, which was dissolved. Insolubles were removed off by filtration while the mixture was hot. The filtrate was cooled with ice to precipitate crystals. The precipitated crystals were collected by filtration to give 2-[[3-methyl-4-(2,2,2-trifluoroethoxy)pyridin-2-yl]methylsulfinyl]-benzimidazole monohydrate, monoethanolate solvate as wet crystals. The crystals were dried at 40° C. for 20 hours in vacuum to give 2-[[3-methyl-4-(2,2,2-trifluoroethoxy) pyridin-2-yl]methylsulfinyl]-benzimidazole as white needles. Yield:7.58 g.(89.0%)
m. p. 177–178° C.(decomp.)
Water content:0.12%
Ethanol content:360 ppm.

REFERENCE EXAMPLE 7

Preparation (1) of an injection containing Compound A

An aqueous solution of sodium hydroxide was added to 15 g. of Compound A, and the mixture was prepared into a solution. To the solution were added 30 g. of mannitol and 5 g. of meglumine, and the mixture was prepared into a solution of 1000 ml. having pH 11.2. The solution was sterilized by filtration by a conventional method. The resultant solution was sealed into ampuls each in an amount of 1 ml. and freeze-dried by a conventional method to prepare freeze-dried product containing Compound A.

In the meantime, 750 g. of macrogol 400 is diluted with water for injection, followed by addition of hydrochloric acid to prepare 2500 ml. of an aqueous solution with pH 4.5. The resultant solution was sterilized by filtration by a conventional method and filled into ampuls in an each amount of 2.5 ml. The ampuls were sealed and sterilized with high pressure steam. For administration, an injection is prepared by adding 2.5 ml. of the macrogol solution to the freeze-dried product containing Compound A and dissolving it.

REFERENCE EXAMPLE 8

Preparation(2) of an injection containing Compound A.

Three hungdred grams of Compound A, 600 g. of mannitol, 100 g. of meglumine and an aqueous solution of sodium hydroxide were mixed by homomixer and solubilized to prepare 20 L. of a solution containing Compound A having pH 11.2. The resultant solution was sterilized by filtration by a conventional method, filled into vials each in an amount of 2 ml. and freeze-dried in a conventional method to prepare freeze-dried product containing Compound A.

In the meantime, 15 kg. of macrogol 400 was diluted with water for injection, followed by addition of hydrochloric acid to prepare 50 L. of an aqueous solution of pH 4.5. The resultant solution was sterilized by filtration in a conventional manner and filled into ampuls each in an amount of 5 ml. The ampuls were sealed and sterilized with high pressure steam. Upon use, 5 ml. of the latter solution is added to the freeze-dried product containing Compound A, and the resultant mixture is prepared into a solution and used.

REFERENCE EXAMPLE 9

Production(3) of an injection containing Compound A.

150 g. of Compound A was mixed with 300 g. of mannitol, followed by addition of an aqueous solution of sodium hydroxide and dissolved it. To the resultant solution was added 50 g. of meglumine, which was dissolved to prepare 10 L. of a solution of pH 11.3 containing Compound A. The resultant solution was sterilized by filtration by a conventional method, filled into vials in an each amount of 4 ml. and freeze-dried by a conventional method to prepare freeze-dried product containing Compound A.

In the meantime, 7.5 kg. of macrogol 400 was diluted with water for injection, followed by addition of hydrochloric acid to prepare 25 L. of an aqueous solution of pH 4.5. The resultant solution was sterilized by filtration by a conventional method, filled into ampuls each in an amount of 10 ml., sealed and sterilized with high pressure steam. Upon administration, injection is prepared by adding 10 ml. of the macrogol solution to the freeze-dried product and dissolving it.

REFERENCE EXAMPLE 10

Preparation of capsules containing Compound A.

Capsules of the formula as indicated in the Table 3 were prepared by the following method with the feed amount (1) or (2) as shown in the Table 1 or Table 2, respectively.

(1) Compoand A and ingredients from the item (3) to (6) were well mixed to prepare powders. (2) Nonpareils were put into a centrifugally fluidized coating granulator(made by Freunt Industry Co. Ltd., CF-1000 in the case of the feed from the Table 2 and CF-1300 in the case of the feed from the Table 3) and coated with the above prepared dusting powder under spraying with an aqueous solution (7) of hydroxypropylcellulose dissolved in purified water.

The resultant spherical granules were dried in vacuum at 40° C. for 16 to 18 hours and sieved (500 $\mu$m and 1190 $\mu$m) to give granules of an active ingredient. Two batches of the granules were put into a Flowcoater(made by Powrex Corp.) and coated with a suspension of (8)methacrylic acid copolymer LD-(12)polysorbate 80 in purified water. To the coated granules was added (13)talc, and the mixture was sieved (600 $\mu$m and 1420 $\mu$m) and dried in vacuum at 42° C. for 16 to 18 hours to give enteric granules.

(14)Talc and (15)light anydride silicic acid were added to 1 batch of the enteric granules(in the processed amount in the Table 2, mixing is possible up to 5 batches, and in the processed amount in Table 3, mixing is possible up to 3 batches). The mixture was prepared into mixed granules by a tumbler mixer(made by Showa Chemical Machinery Co.).

The mixed granules were filled by a capsule filling machine(MG2 Co. or Zanasi Co.) into (16) gelatin capsules No. 1 in an each amount of 30 mg. and into (17)gelatin capsules No. 3 each in an amount of 15 mg.

TABLE 1

| Composition | Processed amount-I<br>Common to 15 mg and 30 mg Capsules |
|---|---|
| Active ingredient granules: | |
| (1) Compound A | 4.481 kg*1 |
| (2) Sucrose.Starch spherical granules (non-pareil) | 15.950 |
| (3) Magnesium carbonate | 3.345*1 |
| (4) Purified sucrose | 8.931*1 |
| (5) Corn starch | 5.436*1 |
| (6) Low substituted hydroxypropylcellulose | 5.974*1 |
| (7) Hydroxypropylcellulose | 0.203 |
| Purified water | (10.297 L) |
| Subtotal | 43.500 kg |
| Enteric granules: | |
| Active ingredient granules | 87.000 kg |
| (8) Methacrylic acid copolymer LD (Eudragit L30D)-55$^R$) | 13.5807*2,*4 |
| | (45.269 kg)*3,*4 |
| (9) Talc | 4.0808*4 |
| (10) Macrogol 6000 | 1.3398*4 |

TABLE 1-continued

Processed amount-I

| Composition | Common to 15 mg and 30 mg Capsules |
|---|---|
| (11) Titanium oxide | 1.3398*4 |
| (12) Polysorbate 80 | 0.690*4 |
| Purified water | (95.004 L)*4 |
| (13) Talc | 0.116 |
| Subtotal | 107.068 kg |

Mixed granules:*5

| | | | | | |
|---|---|---|---|---|---|
| Enteric granules | 107.068 kg | 214.136 kg | 321.204 kg | 428.272 kg | 535.340 kg |
| (14) Talc | 0.058 | 0.116 | 0.174 | 0.232 | 0.290 |
| (15) Light anhydride silicic acid | 0.174 | 0.348 | 0.522 | 0.696 | 0.870 |
| Subtotal | 107.300 kg | 214.600 kg | 321.900 kg | 429.200 kg | 536.500 kg |

Capsules:

| | | | | | |
|---|---|---|---|---|---|
| Mixed granules | 107.300 kg | 214.600 kg | 321.900 kg | 429.200 kg | 536.500 kg |
| (16) Gelatin Capsule No. 1*6 | 290.000 | 580.000 | 870.000 | 1,160.000 | 1,450.000 Cap. |
| (17) Gelatin Capsule No. 3*7 | 580.000 | 1,160.000 | 1,740.000 | 2,320.000 | 2,900.000 Cap. |

*1: More than 3% was processed
*2: Amount of solid
*3: Amount of solution (processed a solution)
*4: Processed more than 5%
*5: Mixing may be possible from 1 to 5 batches of enteric granules
*6: Number of capsules when filled as 30 mg capsule
*7: Number of capsules when filled as 15 mg capsule

TABLE 2

Processed amount-2

| Composition | Common to 15 mg and 30 mg Capsules |
|---|---|
| Active ingredient granules: | |
| (1) Compound A | 6.953 kg*1 |
| (2) Sucrose.Starch spherical granules (non-pareil) | 24.750 |
| (3) Magnesium carbonate | 5.191*1 |
| (4) Purified sucrose | 13.860*1 |
| (5) Corn starch | 8.436*1 |
| (6) Low substituted hydroxypropyl-cellulose | 9.270 |
| (7) Hydroxypropyl-cellulose | 0.315 |
| Purified water | (15.435 L) |
| Subtotal | 67.500 kg |
| Enteric granules: | |
| Active ingredient granules | 135.000 kg |
| (8) Methacrylic acid copolymer LD (Eudragit L30D-55R) | 21.0757*2,*4 (70.250 kg)*3,*4 |
| (9) Talc | 6.332*4 |
| (10) Macrogol 6000 | 2.079*4 |
| (11) Titanium oxide | 2.079*4 |
| (12) Polysorbate 80 | 0.945*4 |
| Purified water | (98.910 L)*4 |
| (13) Talc | 0.180 |
| Subtotal | 166.140 kg |

TABLE 2-continued

Processed amount-2

| Composition | Common to 15 mg and 30 mg Capsules | | |
|---|---|---|---|
| **Mixed granules:*5** | | | |
| Enteric granules | 166.140 kg | 332.280 kg | 498.420 kg |
| (14) Talc | 0.090 | 0.180 | 0.270 |
| (15) Light anhydride silicic acid | 0.270 | 0.540 | 0.810 |
| Subtotal | 166.500 kg | 333.000 kg | 499.500 kg |
| Capsules: | | | |
| Mixed granules | 166.500 kg | 333.000 kg | 499.500 kg |
| (16) Gelatin Capsule No. 1*6 | 450.000 | 900.000 | 1,350.000 Cap. |
| (17) Gelatin Capsule No. 3*7 | 900.000 | 1,800.000 | 2,700.000 Cap. |

*1: More than 3% was processed
*2: Amount of solid
*3: Amount of solution (processed a solution)
*4: Processed more than 5%
*5: Mixing may be possible from 1 to 3 batches of enteric granules
*6: Number of capsules when filled as 30 mg capsule
*7: Number of capsules when filled as 15 mg capsule

TABLE 3

Prescription per one capsule

| Composition | 15 mg Capsule | 30 mg Capsule |
|---|---|---|
| (1) Compound A | 15.0 mg | 30.0 mg |
| (2) Sucrose.Starch spherical granules (non-pareil) | 55.0 | 110.0 |
| (3) Magnesium carbonate | 11.2 | 22.4 |

TABLE 3-continued

Prescription per one capsule

| Composition | 15 mg Capsule | 30 mg Capsule |
|---|---|---|
| (4) Purified sucrose | 29.9 | 59.8 |
| (5) Corn starch | 18.2 | 36.4 |
| (6) Low substituted hydroxypropylcellulose | 20.0 | 40.0 |
| (7) Hydroxypropylcellulose | 0.7 | — |
| Subtotal | 150.0 mg | 300.0 mg |
| Enteric granules: | | |
| Active ingredient granules | 150.0 mg | 300.0 mg |
| (8) Methacrylic acid copolymer (Eudragit L30D-55®) | 22.3 | 44.6 |
| (9) Talc | 6.7 | 13.4 |
| (10) Macrogol 6000 | 2.2 | 4.4 |
| (11) Titanium oxide | 2.2 | 4.4 |
| (12) Polysorbate 80 | 1.0 | 2.0 |
| (13) Talc | 0.2 | 0.4 |
| Subtotal | 184.6 mg | 369.2 mg |
| Mixed granules: | | |
| Enteric granules | 184.6 mg | 369.2 mg |
| (14) Talc | 0.1 | 0.2 |
| (15) Light anhydride silicic acid | 0.3 | 0.6 |
| Subtotal | 185.0 mg | 370.0 mg |
| Capsules: | | |
| Mixed granules | 185.0 mg | 370.0 mg |
| (16) Gelatin Capsule No. 1 | — | 79.0 |
| (17) Gelatin Capsule No. 3 | 50.0 | — |
| Subtotal | 235.0 mg | 449.0 mg |

Industrial Applicability

The present invention provides a method for producing crystals of the benzimidazole compounds substantially solvent-free and of uniform purity, which are of value for medicines such as, for example, anti-ulcer agents, and which is an industrially advantageous method for a large scale production.

The substantially solvent-free crystals which can be produced by the present method are more stable than those hitherto known crystals of solvate, and the degree of decomposition of the compound is extremely low in the course of production step and storage.

We claim:

1. A method for producing a substantially solvent-free crystal of the compound of the formula:

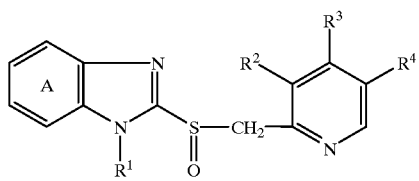

(I)

wherein the ring A may optionally be substituted; $R^1$ represents a hydrogen atom or an N-protecting group; each of $R^2$, $R^3$ and $R^4$ is (1) a hydrogen atom, (2) an alkyl group which may optionally be substituted with halogen atom(s) or (3) an alkoxy group which may optionally be substituted with halogen atom(s) or alkoxy; or its salt, wherein the improvement comprises subjecting water and a $C_{1-6}$ alcohol-solvate crystal of the compound (I) or its salt to being suspended, left standing or stirred in water for a sufficient time, and drying, wherein the water content of the substantially solvent free crystal is less than about 500 ppm and the $C_{1-6}$ alcohol content is less than about 200 ppm.

2. The method as claimed in claim 1, wherein the N-protecting group in the compound (I) is an alkyl group, an acyl group, a carboalkoxy group, a carbamoyl group, an alkylcarbamoyl group, a dialkylcarbamoyl group, an alkyl-carbonylmethyl group, an alkoxycarbonylmethyl group or an alkylsulfonyl group.

3. The method as claimed in claim 1, wherein $R^1$ is a hydrogen atom.

4. The method as claimed in claim 1, wherein the substituent on the ring A of the compound (I) is an alkoxy group which may optionally be substituted by halogen.

5. The method as claimed in claim 1, wherein the ring A of the compound (I) is unsubstituted.

6. The method as claimed in claim 1, wherein $R^2$ is methyl or methoxy, $R^2$ is (1) $C_{1-4}$ alkoxy which may optionally be substituted by fluorine(s) or (2) $C_{1-4}$ alkoxy-$C_{1-8}$ alkoxy, $R^4$ is a hydrogen atom or methyl.

7. The method as claimed in claim 1, wherein the compound (I) is 2-[[3-methyl-4-(2,2,2-trifluoroethoxy)-pyridin-2-yl]methylsulfinyl]benzimidazole or its salt.

8. The method as claimed in claim 1, wherein the $C_{1-6}$ alcohol-solvate is ethanol.

9. The method as claimed in claim 1, wherein the solvate crystals are obtained by recrystallization from an aqueous $C_{1-6}$ alcohol.

10. The method as claimed in claim 1, wherein the aqueous $C_{1-6}$ alcohol contains about 2 to about 30 parts by volume of $C_{1-6}$ alcohol for each part by volume of water.

11. The method as claimed in claim 1, wherein the aqueous $C_{1-6}$ alcohol contains about 5 to about 15 parts by volume of $C_{1-6}$ alcohol for each part by volume of water.

12. The method as claimed in claim 1, wherein the aqueous $C_{1-6}$ alcohol contains 9 parts by volume of $C_{1-6}$ alcohol for each part by volume of water.

13. The method as claimed in claim 1, wherein the water to be used for transforming of crystalline form is used in a proportion of about 2 to about 20 parts by volume relative to the solvate crystals.

14. The method as claimed in claim 1, wherein the water to be used for transforming of crystalline form is used in a proportion of about 5 to about 10 parts by volume relative to the solvate crystals.

15. The method as claimed in claim 1, wherein the water temperature ranges from about 15° C. to about 90° C.

16. The method of claim 1, wherein the water content is not higher than about 300 ppm.

17. The method of claim 1, wherein the water content is not higher than about 200 ppm and the $C_{1-6}$ alcohol content is not higher than about 100 ppm.

* * * * *